US012788771B2

(12) United States Patent
Oberg

(10) Patent No.: US 12,788,771 B2
(45) Date of Patent: Nov. 10, 2026

(54) MIV-818/LENVATINIB COMBINATION THERAPY FOR LIVER CANCER

(71) Applicant: MEDIVIR AB, Huddinge (SE)

(72) Inventor: Fredrik Oberg, Huddinge (SE)

(73) Assignee: MEDIVIR AB, Huddinge (SE)

( * ) Notice: Subject to any disclaimer, the term of this patent is extended or adjusted under 35 U.S.C. 154(b) by 1001 days.

(21) Appl. No.: 17/919,221

(22) PCT Filed: Apr. 14, 2021

(86) PCT No.: PCT/SE2021/050338
§ 371 (c)(1),
(2) Date: Jul. 14, 2023

(87) PCT Pub. No.: WO2021/211039
PCT Pub. Date: Oct. 21, 2021

(65) Prior Publication Data

US 2024/0024342 A1 Jan. 25, 2024

(30) Foreign Application Priority Data

Apr. 15, 2020 (SE) .................................. 2050430-4

(51) Int. Cl.
*A61K 31/688* (2006.01)
*A61K 31/47* (2006.01)
*A61P 35/00* (2006.01)

(52) U.S. Cl.
CPC ............ *A61K 31/688* (2013.01); *A61K 31/47* (2013.01); *A61P 35/00* (2018.01)

(58) Field of Classification Search
CPC ........ A61K 31/688; A61K 31/47; A61P 35/00
See application file for complete search history.

(56) References Cited

U.S. PATENT DOCUMENTS

| | | | |
|---|---|---|---|
| 10,960,017 B2 * | 3/2021 | Albertella et al. |
| 12,303,521 B2 * | 5/2025 | Albertella et al. |
| 2019/0091246 A1 * | 3/2019 | Albertella et al. |

FOREIGN PATENT DOCUMENTS

| | | |
|---|---|---|
| CN | 110831597 A | 2/2020 |
| EP | 1415987 B1 | 2/2007 |

(Continued)

OTHER PUBLICATIONS

Al-Salama et al. (Drugs (2019); 79:665-674) (Year: 2019).*

(Continued)

*Primary Examiner* — Brandon J Fetterolf
(74) *Attorney, Agent, or Firm* — Susan W. Gorman; Intelink Law Group, PC

(57) ABSTRACT

Use of lenvatinib, or a pharmaceutically acceptable salt thereof in combination with a compound of the formula MIV-818:

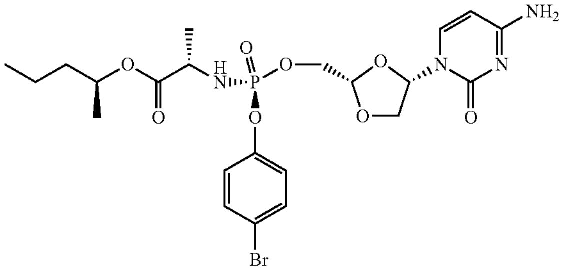

Figure 1A:
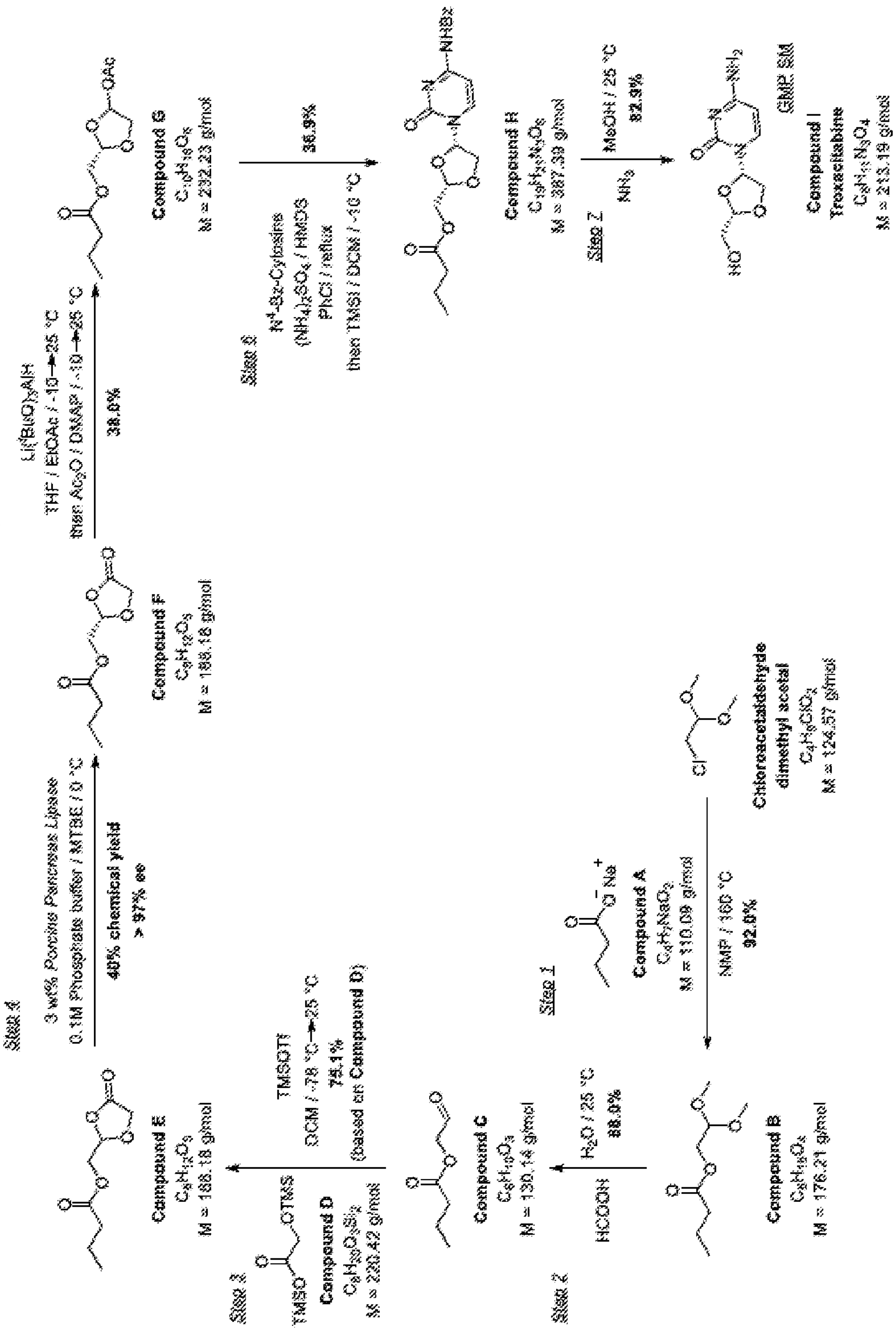

or pharmaceutically acceptable salt thereof, in the treatment of liver cancer or liver metastases. The respective dosage regimes of the compounds can be delivered concurrently or alternately.

12 Claims, 3 Drawing Sheets

(56) References Cited

FOREIGN PATENT DOCUMENTS

| | | | |
|---|---|---|---|
| JP | 7709456 | B | 7/2025 |
| KR | 20180118745 | A | 10/2018 |
| WO | 2005063713 | A1 | 7/2005 |
| WO | 2016030335 | A1 | 3/2016 |
| WO | 2016031841 | A1 | 3/2016 |
| WO | 2017151044 | A1 | 9/2017 |

OTHER PUBLICATIONS

Bethell, R et al, "Liver-targeting with the novel nucleotide prodrug MIV-818 designed for the treatment of liver cancers." EASL Poster, (2017).

Bethell, R et al, "Selective targeting of the liver with the nucleotide prodrug MIV-818 for the treatment of liver cancers." Hepatol Int (2017) 11 (Suppl 1):S1-S1093.

International Search Report issued on May 28, 2021 for corresponding PCT application No. PCT/SE2021/050338.

Kim, J et al, "Lenvatinib Versus Sorafenib as First-Line Treatment of Unresectable Hepatocellular Carcinoma: A Cost—Utility Analysis." The Oncologist (2020) vol. 25:e512-e519 www.TheOncologist.com.

Rizoska, B. et al "Abstract 2930: Synergistic and additive anti-tumor effects of MIV-818 in combination with sorafenib in nonclinical hepatocellular carcinoma models", AACR Annual Meeting (2018).

International Preliminary Report on Patentability issued on May 30, 2022 for corresponding PCT application No. PCT/SE2021/050338.

Grove et al, "Anticancer Activity of Beta-L-Dioxolane-cytidine, a Novel Nucleoside Analogue with the Unnatural L Configuration", Cancer Res., 1995, vol. 55, pp. 3008-3011.

Herver, Christina, "Medivir—focusing on cancer one prodrug at a time", https://www.nature.com/articles/d43747-020-00853-3, Biopharma Dealmakers (Biopharm Deal), ISSN 2730-6283 (online), Mar. 2020.

Communication under Rule 71(3) EPC—Intent to Grant with Application Text in corresponding EP application (EP21787576) from the European Patent Office on Oct. 11, 2024.

Decision to grant a European patent pursuant to Article 97(1) EPC, issued in corresponding EP application (EP21787576) from the European Patent Office on Feb. 20, 2025.

Extended Search Report issued in corresponding EP application (EP21787576) from the European Patent Office on Mar. 18, 2024.

Notice of Allowance and translation for corresponding JP application (JP2022-562676) from the Japanese Patent Office on Jun. 30, 2025.

Office Action and translation issued in corresponding JP application (JP2022-562676) from the Japanese Patent Office on Feb. 20, 2025.

Notification of Patent Registration and translation issued in corresponding JP application (JP2022-562676) from the Japanese Patent Office on Jul. 8, 2025.

Office Action issued from Korean Intellectual Property Office on May 6, 2026, in corresponding Korean national phase application No. 10-2022-7039743 with machine translation.

* cited by examiner

Compound E
$C_8H_{12}O_5$
M = 188.18 g/mol

Compound F
$C_8H_{12}O_5$
M = 188.18 g/mol

Compound G
$C_{10}H_{16}O_6$
M = 232.23 g/mol

Compound D
$C_8H_{20}O_3Si_2$
M = 220.42 g/mol

Compound C
$C_6H_{10}O_3$
M = 130.14 g/mol

Compound H
$C_{19}H_{21}N_3O_6$
M = 387.39 g/mol

Compound A
$C_4H_7NaO_2$
M = 110.09 g/mol

Compound B
$C_8H_{16}O_4$
M = 176.21 g/mol

Chloroacetaldehyde dimethyl acetal
$C_4H_9ClO_2$
M = 124.57 g/mol

Compound I
Troxacitabine
$C_8H_{11}N_3O_4$
M = 213.19 g/mol

MIV-818/LENVATINIB COMBINATION THERAPY FOR LIVER CANCER

This Non-Provisional application is a National Phase Under 35 USC § 371 of PCT International Application No. PCT/SE2021/050338 filed on Apr. 14, 2021, which claims priority under 35 U.S.C. § 119 on Patent Application No. 2050430-4 filed in Sweden on Apr. 15, 2020, the entire contents of each of which are hereby incorporated by reference.

FIELD OF THE INVENTION

The invention relates to combination therapy for cancer, and more specifically to treatment regimes and products employing the kinase inhibitor lenvatinib and the troxacitabine phosphoramidate nucleotide MIV-818 for liver cancer and liver metastases.

BACKGROUND OF THE INVENTION

Liver cancer (or hepatic cancer) is a cancer that originates in the liver. Primary liver cancer is the fifth most frequently diagnosed cancer globally and the second leading cause of cancer death. Liver cancers are malignant tumours that grow on the surface or inside the liver. They are formed from either the liver itself or from structures within the liver, including blood vessels or the bile duct.

The leading cause of liver cancer is viral infection with hepatitis B virus or hepatitis C virus. The cancer usually forms secondary to cirrhosis caused by these viruses. For this reason, the highest rates of liver cancer occur where these viruses are endemic, including East-Asia and sub-Saharan Africa. Liver cancers should not be confused with liver metastases, also known as secondary liver cancer, which is a cancer that originate from organs elsewhere in the body and migrate to the liver.

The most frequent liver cancer, accounting for approximately 75% of all primary liver cancers, is hepatocellular carcinoma (HCC). HCC is a cancer formed by liver cells, known as hepatocytes that become malignant. Another type of cancer formed by liver cells is hepatoblastoma, which is specifically formed by immature liver cells. It is a rare malignant tumour that primarily develops in children, and accounts for approximately 1% of all cancers in children and 79% of all primary liver cancers under the age of 15.

Liver cancer can also form from other structures within the liver such as the bile duct, blood vessels and immune cells. Cancer of the bile duct (cholangiocarcinoma and cholangiocellular cystadenocarcinoma) accounts for approximately 6% of primary liver cancers. There is also a variant type of HCC that consists of both HCC and cholangiocarcinoma. Tumours of the liver blood vessels include angiosarcoma and hemangioendothelioma. Embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumours, carcinoid tumours and lymphomas. Lymphomas usually have diffuse infiltration to liver, but it may also form a liver mass in rare occasions.

Surgical resection is often the treatment of choice for non-cirrhotic livers. Increased risk of complications such as liver failure can occur with resection of cirrhotic livers. 5-year survival rates after resection has massively improved over the last few decades and can now exceed 50%. Recurrence rates after resection due to the spread of the initial tumour or formation of new tumours exceeds 70%. Liver transplantation can also be used in cases of HCC where this form of treatment can be tolerated and the tumour fits specific criteria (e.g., the Milan criteria). Less than 30-40% of individuals with HCC are eligible for surgery and transplant because the cancer is often detected late stage. Also, HCC can progress during the waiting time for liver transplants, which can ultimately prevent a transplant.

Percutaneous ablation is the only non-surgical treatment that can offer cure. There are many forms of percutaneous ablation, which consist of either injecting chemicals into the liver (ethanol or acetic acid) or producing extremes of temperature using radio frequency ablation, microwaves, lasers or cryotherapy. Of these, radio frequency ablation has one of the best reputations in HCC, but the limitations include inability to treat tumours close to other organs and blood vessels due to heat generation and the heat sync effect, respectively.

Few systemic chemotherapeutics are available for HCC, although local chemotherapy may be used in a procedure known as transarterial chemoembolization (TACE). In this procedure, cytotoxic drugs such as doxorubicin or cisplatin with lipiodol are administered and the arteries supplying the liver are blocked by gelatine sponge or other particles.

Radiotherapy is not often used in HCC because the liver is not tolerant to radiation. Even with modern technology providing well targeted radiation to specific areas of the liver, collateral damage to surrounding liver tissue is a problem, emphasizing the need for better, "liver sparing" regimens. Dual treatments of radiotherapy plus chemoembolization, local chemotherapy, systemic chemotherapy or targeted therapy drugs may show benefit over radiotherapy alone.

Lenvatinib (developed and marketed by Eisai in various countries as Lenvima® or Lenvanix®), is an FDA-approved drug predominantly for patients with thyroid and renal cell carcinoma, but also for a restricted subset of hepatocellular carcinoma patients that cannot be removed surgically in patients who have not received therapy by mouth or injection.

Lenvatinib has the chemical structure depicted below and is generally presented as the mesylate salt.

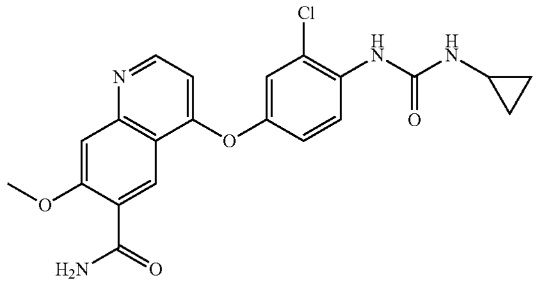

Lenvatinib is an orally administered small molecule interacting with multiple intracellular and cell surface kinases including the vascular endothelial growth factor receptors VEGFR1, VEGFR2 and VEGFR3, as well as fibroblast growth factor receptor FGFR1, FGFR2, FGFR3 and FGFR4, platelet-derived growth factor pathway receptor alpha PDGFRα, c-KIT and the RET oncogene. Not unexpectedly with such a diverse range of inhibitions, side effects such as QT prolongation and hypertension restrict the adoption of lenvatinib treatments. By inhibiting the kinases recited above, genetic transcription involving cell proliferation and angiogenesis is inhibited, with the intriguing observation that hypoxia in solid tumour tissues may be increased due to the treatment reducing blood supply to the tumour. However, even with the development of drugs like lenvatinib, the current treatment options for liver cancer are insufficient due to its limited effectiveness and severe side effects/toxicities.

A preferred salt and polymorph of lenvatinib is shown in WO2005/063713. An enhanced purity preparation method is shown in WO2016/031841. The technical content of these three patent specifications is incorporated herein.

Troxacitabine, (beta-L-dioxolane cytidine) is a cytotoxic deoxycytidine analogue with an unnatural L-configuration which has demonstrated broad activity against both solid and hematopoietic malignancies in vitro and in vivo. Particularly, impressive activity has been observed against human cancer cell lines and xenografts of hepatocellular, prostate, and renal origin (Cancer Res., 55, 3008-3011, 1995). Troxacitabine treatment has shown to give rise to a resistance mutation of the kinase deoxycytidine kinase (dCK) which is normally responsible for the first phosphorylation step of the nucleoside, leading to no or very low levels of troxacitabine monophosphate.

Troxacitabine entered phase III clinical trials in 2008 in the acute myelogenous leukemia indication, but did not proceed to registration. Discontinued phase II trials with troxacitabine include breast cancer, colorectal cancer, pancreatic cancer, melanoma, NSCLC, renal, prostate and ovarian tumours. Troxacitabine was generally administered as an intravenous infusion, thereby exposing many tissues to the drug, irrespective of the site of the cancer. It is believed that the clinical development of troxacitabine has been abandoned. MIV-818 is an orally administered nucleotide derivative of troxacitabine with the formula:

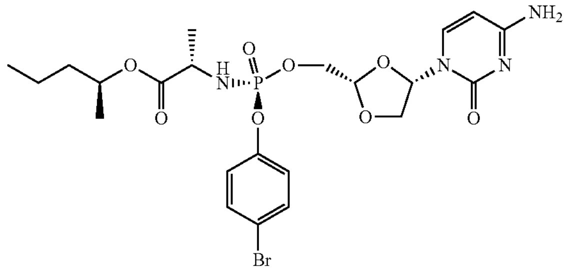 [SMILES: CCC[C@H](C)OC(=O)[C@H](C)N[P@](=O)(OC[C@H]1OC[C@@H](n2ccc(N)nc2=O)O1)Oc1ccc(Br)cc1]

The orally administered MIV-818 enters the hepatic portal from the gut and is thus delivered direct to the liver, where it is adsorbed intracellularly in liver cells and unmasked to the nucleotide monophosphate precursor. The highly charged nucleotide precursor and the corresponding intracellularly generated triphosphate active species are trapped within the liver cells, with the corollary that the troxacitabine nucleoside is not released systemically to any great extent. In other words MIV-818 is targeted to, and concentrated in, the very tissue which it is destined to treat, whereas exposure of other tissues to the toxic metabolite troxacitabine is substantially reduced. General methodology for the preparation of MIV-818 is shown in WO2016/03033S whose technical disclosure is incorporated herein. A favoured synthesis route is depicted on FIGS. 1A and 1B herein.

SUMMARY OF THE INVENTION

The invention is based, at least in part, on the discovery that certain treatment combinations of lenvatinib and MIV-818 are particularly effective at inhibiting, and preventing the proliferation of, liver cancer cells. This discovery can be described as a synergy, or greater than additive effect, that is specific to lenvatinib and MIV-818, within the area of liver cancer (e.g., HCC).

We hypothesise that this beneficial interaction may even extend to the treatment of liver metastases, that is to say other cancer types which spread from their primary tissue to the liver.

Without wishing to be bound by theory, we hypothesise that the angiogenesis inhibition afforded by lenvatinib, will induce migration of T-cell populations into the cancerous tissue. Serendipitously, these T cells, notably T-effector cells, will be stimulated to attack cancerous tissue by IL-2 generation elicited in situ in the liver by concomitant or staggered MIV-818 administration. A further serendipitous interaction between lenvatinib and MIV-818, arises due to the anti-angiogenesis activity of lenvatinib which is believed to generate local hypoxia in hepatic tissues by restricting blood flow into solid tumours. This hypoxia in turn increases the metabolic activation of the troxacitabine prodrug to its cytotoxic triphosphate, thereby contributing to the anticarcinogenic efficacy of the claimed combination therapy.

Again, without wishing to be bound by theory it is expected that the interaction between lenvatinib and MIV-818, each orally administered, will have a mechanistic resemblance to the interaction between lenvatinib and pembrolizumab, as regards migration and in situ stimulation of T cell populations. In contrast, however, pembrolizumab is a monoclonal antibody which must be dosed intravenously in a hospital setting with a rigorous temperature controlled supply chain, and is orders of magnitude more difficult and expensive to manufacture compared with MIV-818.

Accordingly, the invention provides methods, treatment regimes and compositions for treating liver cancer and liver metastases, whereby lenvatinib and MIV-818, are administered in combination (as defined herein) to human or mammalian individuals.

The EMA and FDA approved daily dose for lenvatinib in HCC is 8 mg (<60 kg) or 12 mg (>60 kg) daily, (2 or 3×4 mg hard capsules), but an extensive dose reduction scheme is mandated in the Summary of Product Characteristics.

As clinical experience with MIV-818 is thus far quite limited, no approved does is yet available, but scaling from animal species and preliminary phase 1 clinical trial data, are consistent with a likely daily dose for a nn kg human in the range nn to nn mg/day, for example nn to nn mg/day.

A person of ordinary skill will understand that lenvatinib and MIV-818 dosage and administration can follow medically approved guidelines, as well as medically accepted deviations or alterations to such guidelines. Further description and details on lenvatinib and MIV-818 dosing and administration in the context of the invention are provided in the Combination Chemotherapy section below.

An embodiment of the invention provides a method or treatment regime for the treatment of liver cancer in a human or mammalian subject, which method comprises the simultaneous, separate, staggered or combined unit-dosage administration of an effective amount of MIV-818 and an effective amount of lenvatinib to the subject. Preferably both MIV-818 and lenvatinib are dosed orally. The treatment regime may consist of a plurality of distinct cycles of MIV-818 and of lenvatinib, optionally separated by day, week or month-long treatment holidays. Alternatively the MIV-818 and lenvatinib are each administered daily (ie QD, BiD or TiD or every second day) to the subject so that the liver is exposed to both active ingredients part or all of the same time interval.

Liver Cancer

The invention, in various aspects and embodiments, is applicable to the treatment of liver cancer in a subject, which can be a primate, such as a human. The subject can be a mammal, such as mammal other than a mouse. The subject can be an adult human (i.e., 18 years or older), or a juvenile human (i.e., less than 18 years old).

In various embodiments, the liver cancer (e.g., HCC) is not resistant to lenvatinib. Alternatively, the liver cancer (e.g., HCC) can have primary or secondary resistance to lenvatinib, which is reversed or ameliorated by the combination therapy of the invention. Accordingly, the subject can be a responder to lenvatinib in the absence of MIV-818. The subject can be a non-responder to lenvatinib in the absence of MIV-818. In some embodiments, the subject has undergone a prior treatment with lenvatinib lasting at least 2, 4, 6, 8, 10 months or longer. In other embodiments, the subjects are patients who have experienced one or more significant adverse side effect to lenvatinib and therefore require a reduction in dose.

In various embodiments, the liver cancer (e.g., HCC) is intermediate, advanced, or terminal stage. The liver cancer (e.g., HCC) can be metastatic or non-metastatic. The liver cancer (e.g., HCC) can be resectable or unresectable. The liver cancer (e.g., HCC) can comprise a single tumour, multiple tumours, or a poorly defined tumour with an infiltrative growth pattern (into portal veins or hepatic veins). The liver cancer (e.g., HCC) can comprise a fibrolamellar, pseudoglandular (adenoid), pleomorphic (giant cell), or clear cell pattern. The liver cancer (e.g., HCC) can comprise a well differentiated form, and tumour cells resemble hepatocytes, form trabeculae, cords, and nests, and/or contain bile pigment in cytoplasm. The liver cancer (e.g., HCC) can comprise a poorly differentiated form, and malignant epithelial cells are discohesive, pleomorphic, anaplastic, and/or giant. In some embodiments, the liver cancer (e.g., HCC) is associated with hepatitis B, hepatitis C, cirrhosis, or type 2 diabetes.

In some embodiments, the subject is a human having an Eastern Cooperative Oncology Group (ECOG) performance status <2.

In some embodiments, the subject is a human having acceptable liver function defined as (i) total bilirubin <1.5 times the upper limit of normal (ULN); for patients with hepatocellular carcinoma only, total bilirubin <3 mg/dL (i.e., Child-Pugh Score for bilirubin is no greater than 2); (ii) aspartate aminotransferase (AST), alanine aminotransferase (ALT) and alkaline phosphatase (ALP)<5×ULN; or (iii) acceptable renal function: ·Serum creatinine <1.5 times the ULN, or calculated creatinine clearance >60 mL/min/1.73 $m^2$ for patients with creatinine levels above 1.5 times the institutional normal.

In some embodiments, the subject is a human having acceptable haematological status defined as (i) absolute Neutrophil Count (ANC)>1500 cells/$mm^3$; (ii) platelet count >100,000 pits/$mm^3$ (without transfusion); >75,000 pits/$mm^3$ for patients with hepatocellular carcinoma only; or (iii) haemoglobin >9 g/dL.

In some embodiments, the subject is a human having a prothrombin time (PT) or International Normalized Ratio (INR)<1.25×ULN; INR <1.7 or prothrombin time (PT) or <4 seconds above ULN (i.e., Child-Pugh Score is no greater than 1 for the coagulation parameter); or serum albumin >2.8 g/dL (i.e., Child-Pugh Score for albumin is no greater than 2).

In some embodiments, the subject is a human having a prothrombin Child-Pugh Class A (score 5-6) disease. Score for hepatic encephalopathy must be 1; the score for ascites must be no greater than 2 and clinically irrelevant; for the determination of the Child-Pugh Class.

In some embodiments, the subject is a human that does not have a New York Heart Association (NYHA) Class Ill or IV cardiac disease, myocardial infarction within the past 6 months, unstable and/or symptomatic arrhythmia, or evidence of ischemia on ECG.

In some embodiments, the subject does not have an active, uncontrolled bacterial, viral, or fungal infections requiring systemic therapy.

In some embodiments, the subject is a human that is not a pregnant or nursing woman.

In some embodiments, the subject is a human that does not have a known infection with human immunodeficiency virus (HIV).

In some embodiments, the subject is a human that does not have a serious non-malignant disease (e.g., hydronephrosis, liver failure, or other conditions) that could compromise the therapy.

In some embodiments, the subject is a human that does not have a recent history of haemorrhage and patients predisposed to haemorrhage due to coagulopathies or structural anomalies.

In some embodiments, the subject is a human that does not require treatment with therapeutic doses of coumarin-type anticoagulants.

In some embodiments, the subject is a human that does not have a cirrhosis classed as Child-Pugh B or C.

In some embodiments, the subject is a human that wherein the subject has an alpha-fetoprotein (AFP)>10, 50, 100, 200, 300, 400, or 500 ng/ml.

In some embodiments, the subject is a human that wherein the subject has an elevates (>10%) AFP-L3 level.

In some embodiments, the subject is a human that has a Des-Gamma-Carboxy (Abnormal) Prothrombin (DCP)>5, 7.5, 10, 25, 50, 75, or 100 ng/mL.

In some embodiments, the subject is a human that has an abnormal level of an epidermal growth factor receptor (EGFR) (erbB-1), c-erb-2 (Her-2/neu), c-erb-3 (HER-3), c-erb-4 (HER-4), or a combination thereof. In some embodiments, the subject is a human that has an abnormal level of Alpha-Fetoprotein (AFP); Glypican-3 (GPC3); Des-Gamma-Carboxy (Abnormal) Prothrombin (DCP); Serum gamma-glutamyl transferase (GGT); Alpha-I-fucosidase (AFU); Human Carbonyl Reductase 2; Golgi phosphoprotein 2 (GOLPH2); Transforming Growth Factor-Beta (TGF-Beta); Tumor-Specific Growth Factor (TSGF); Hepatocyte growth factor/scatter factor (HGF/SF); Basic Fibroblast Growth Factor; Alpha-Fetoprotein mRNA (AFP mRNA); Gamma-Glutamyl Transferase mRNA (GGT mRNA); Insulin-Like Growth Factor II (IGF-II) mRNA; Albumin mRNA; DK 1; Golgi protein 73 (GP73); Protein induced by vitamin K absence or antagonist II (PIVKA-II); miR-122, miR-192, miR-21, miR-223, miR-26a, miR-27a, and miR-801, or a combination thereof.

In various embodiments, any of the aspects and embodiments can be combined with any one or more of the features below. For example:

In some embodiments, the liver cancer is primary liver cancer.

In some embodiments, the liver cancer is hepatocellular carcinoma (HCC).

In some embodiments, the liver cancer is intra-hepatic cholangiocarcinoma.

In some embodiments the liver metastasis is derived from colorectal cancer, but also breast cancer, esophageal cancer, lung cancer, melanoma, pancreatic cancer, and stomach cancer.

Combination Chemotherapy

As used herein, the term "administration in combination" is not limited to the situation where both the lenvatinib and MIV-818 are co-administered to the human or mammal in a common dosage unit such as a tablet or oral suspension, although such common dosage units can have advantages in terms of dosing convenience, patient compliance and accuracy of dose.

More typically the lenvatinib and MIV-818 are presented in respective dosage units, allowing the prescribing physician greater freedom of calibration of dose. In the case of lenvatinib, commercially available products currently include 4 mg and 10 mg hard capsules.

The lenvatinib dosing amount and/or schedule can follow clinically approved, or experimental, guidelines. In various embodiments, the dose of lenvatinib is about 4-12 mg/day, or dosed every second day, as specified by the SPC. Individuals with low body weights such as juveniles and geriatrics may require dosing with partial capsules.

The MIV-818 will generally be administered orally, most typically as one or several tablets or capsules, each containing between 10 mg to 600 mg of the active pharmaceutical ingredient. Representative tablets or capsules may contain between 25 mg and 500 mg, or between 50 mg and 450 mg, or between 100 mg and 400 mg, such as between 150 mg and 400 mg, between 200 mg and 500 mg or between 250 mg and 500 mg.

In various embodiments the MIV-818 is administered to the subject in 1, 2, 3, 4, 5, 6, or 7 daily doses over a single week (7 days). The MIV-818 can be administered to the subject in 1, 2, 3, 4, 5, 6, 7, 8, 9, 10, 11, 12, 13, or 14 daily doses over 14 days. The MIV-818 can be administered to the subject in 1, 2, 3, 4, 5, 6, 7, 8, 9, 10, 11, 12, 13, 14, 15, 16, 17, 18, 19, 20, or 21 daily doses over 21 days. The MIV-818 can be administered to the subject in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In various embodiments, the MIV-818 is administered for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); 1 week with 3 consecutive weeks off (total 28 days).

In various embodiments, the MIV-818 is administered on day 1 of a 7,14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. The MIV-818 can be administered once every 1, 2, 3, 4, 5, 6, 7, or 8 weeks.

The lenvatinib and MIV-818 may be administered substantially simultaneously, as a common dosage unit or respective dosage unit, or the administration in combination may be staggered or alternating, that is with separate cycles of lenvatinib and the MIV-818. For example, serial week long cycles of daily lenvatinib, may be interspersed with one, two, three, five or seven day cycles of daily MIV-818.

Alternatively, a loading dose of one agent, for example the lenvatinib component, may be commenced, for example to impact angiogenesis in the tumour and/or build up local hypoxia in the liver, followed by commencement of co-dosing with MIV-818.

It may be convenient to monitor staggered combination administration by reference to a target molar or mg ratio between lenvatinib and the MIV-818. In various embodiments, the ratio (e.g., molar ratio of lenvatinib: MIV-818) is typically between about 20:1 to 1:20, such as 5:1, 2:1, 1:1, 1:2, 1:5 or 1:10.

The molar ratio of lenvatinib: MIV-818 can be measured over different periods of time. For example, the molar ratio can be the amount of lenvatinib: MIV-818 administered to the subject in a single day, a single week, 14 days, 21 days, or 28 days.

According to certain embodiments the method of the invention envisages that the lenvatinib and the MIV-818 components are each administered daily (as QD, BID or TID) on the same day.

In such an embodiment the lenvatinib and the MIV-818 may be co-delivered in a common, orally administered dosage unit, such as a capsule, softgel capsule or tablet In other embodiments the method of the invention envisages that the lenvatinib and the MIV-818 are administered as separate, orally administered dosage units.

In a representative embodiment of the paragraph immediately above, the dosage unit(s) of lenvatinib and the dosage unit(s) of the MIV-818 are administered at least 6 hours apart on any given day, preferably at least 8 hours and typically around 12 hours apart, for patient comfort.

Certain embodiments of the method of the invention envisage that the lenvatinib and the MIV-818 are alternately administered in monotherapy treatment cycles of 1-28 days, optionally interspersed with treatment-free periods of 1-28 days.

As used herein "monotherapy" of the lenvatinib or the MIV-818 components means that lenvatinib is not administered during a cycle of the MIV-818 and vice versa. Monotherapy does not preclude the co-administration of other therapeutics (including other anticancer agents or palliatives, all as ordained by the responsible physician).

As used herein for describing ranges, e.g., of ratios, doses, times, and the like, the terms "about" embraces variations that are within the relevant margin of error, essentially the same (e.g., within an art-accepted confidence interval such as 95% for phenomena that follow a normal or Gaussian distribution), or otherwise does not materially change the effect of the thing being quantified.

A course of lenvatinib-MIV-818 therapy can be prescribed by a clinician. The MIV-818 component (and hence the combination therapy) can be administered for 1, 2, 3, 4, 5, 6, 7, 8, 9, 10, 11, or 12 cycles.

A course of lenvatinib-MIV-818 therapy can be continued until a clinical endpoint is met. In some embodiments, the therapy is continued until disease progression or unacceptable toxicity occurs. In some embodiments, the therapy is continued until achieving a pathological complete response (pCR) rate defined as the absence of liver cancer (e.g., HCC). In some embodiments, the therapy is continued until partial or complete remission of the liver cancer. Administering the MIV-818 and the lenvatinib to a plurality of subjects having HCC is believed to increase the Overall Survival (OS), the Progression free Survival (PFS), the Disease Free Survival (DFS), the Response Rate (RR), the Quality of Life (QoL), or a combination thereof.

In various embodiments, the treatment reduces the size and/or number of the liver cancer tumour(s). The treatment can prevent the liver cancer tumour(s) from increasing in size and/or number. The treatment can prevent the liver cancer tumour(s) from metastasizing.

In the methods of the invention, administration is not limited to any particular delivery system and may include, without limitation, parenteral (including subcutaneous, intravenous, intramedullary, intraarticular, intramuscular, or intraperitoneal injection), rectal, topical, transdermal, or preferably oral (for example, in capsules, suspensions, or tablets).

Administration to an individual may occur in a single dose or in repeat administrations, and in any of a variety of physiologically acceptable salt forms, and/or with an acceptable pharmaceutical carrier and/or additive as part of a pharmaceutical composition.

Physiologically acceptable salt forms and standard pharmaceutical formulation techniques, dosages, and excipients are well known to persons skilled in the art (see, e.g., Physicians' Desk Reference (PDR®) 2005, 59th ed., Medical Economics Company, 2004; and Remington: The Science and Practice of Pharmacy, eds. Gennado et al. 21th ed., Lippincott, Williams & Wilkins, 2005).

Additionally, effective dosages achieved in one animal may be extrapolated for use in another animal, including humans, using conversion factors known in the art. See, e.g., Freireich et al., Cancer Chemother Reports 50 (4): 219-244 (1966) and the table below for equivalent surface area dosage factors).

Equivalent surface area dosage factors

| | From: | | | | |
|---|---|---|---|---|---|
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The combination therapies of the invention are not specifically limited to any particular course or regimen and may be employed separately or in conjunction with other therapeutic modalities (e.g. chemotherapy or radiotherapy).

A combination therapy in accordance with the present invention can include additional therapies (e.g. pharmaceutical, radiation, and the like) beyond the lenvatinib and MIV-818. Similarly, the present invention can be used as an adjuvant therapy (e.g., when combined with surgery). In various embodiments, the subject is also treated by surgical resection, percutaneous ethanol or acetic acid injection, transarterial chemoembolization, radiofrequency ablation, laser ablation, cryoablation, focused external beam radiation stereotactic radiotherapy, selective internal radiation therapy, intra-arterial iodine-131-lipiodol administration, and/or high intensity focused ultrasound.

The combination of MIV-818 and lenvatinib can be used as an adjuvant, neoadjuvant, concomitant, concurrent, or palliative therapy. The combination of MIV-818 and lenvatinib can be used as a first line therapy, second line therapy, or crossover therapy.

In some embodiments, the therapeutically effective dose of lenvatinib may be reduced through combination with MIV-818. For example, the weekly or monthly dose of lenvatinib may be reduced by at least 10%, 20%, 30%, 40%, 50%, 60%, 70%, 80%, 90% or more relative to the maximum recommended dose or the maximum tolerated dose. In other embodiments, lenvatinib may be administered at an effective dose that is at least 50%, 60%, 70%, 80%, 90% or more below the dose needed to be effective in the absence of the MIV-818 administration. In some embodiments, the $IC_{50}$ of lenvatinib is reduced by at least 4—, 5-, 10-, 20-, 30-, 40-, 50-, or 100-fold relative to the $IC_{50}$ in the absence of MIV-818.

It is understood that isotopic variants of MIV-818 and/or lenvatinib wherein one or more of the atom(s) is/are replaced by an isotope of that/these atom(s), i.e. an atom having the same atomic number but an atomic mass different from the one(s) typically found in nature are within the scope of the invention when administered in combination, as provided herein. Examples of isotopes that may be incorporated into MIV-818 and/or lenvatinib, include but are not limited to isotopes of hydrogen, such as $^{2}H$ and $^{3}H$ (also denoted D for deuterium and T for tritium, respectively), carbon, such as $^{11}C$, $^{13}C$ and $^{14}C$, nitrogen, such as $^{13}N$ and $^{15}N$, oxygen, such as $^{15}O$, $^{17}O$ and $^{18}O$, phosphorus, such as $^{31}P$ and $^{32}P$, fluorine, such as $^{18}F$, chlorine, such as $^{36}Cl$ and bromine such as $^{75}Br$, $^{76}Br$, $^{77}Br$ and 82Br. Isotopically labelled compounds include for example those wherein radioactive isotopes, such as $^{3}H$ and $^{14}C$ are present, or those wherein non-radioactive isotopes, such as $^{2}H$ and $^{13}C$ are present.

The choice of isotope included in an isotope-containing compound will depend on the specific application of that compound. For example, for drug or substrate tissue distribution assays or in metabolic studies compounds wherein a radioactive isotope such as $^{3}H$ or $^{14}C$ is incorporated, will generally be most useful. For radio-imaging applications, for example positron emission tomography (PET) a positron emitting isotope such as $^{11}C$, $^{18}F$, $^{13}N$ or $^{15}O$ will be useful. The incorporation of a heavier isotope, such as deuterium, i.e. $^{2}H$, may provide certain therapeutic advantages resulting from greater metabolic stability to a compound of the invention, which may result in, for example, an increased in vivo half life of the compound, reduced dosage requirements or an improvement in therapeutic index.

Isotopically-labelled variants of MIV-818 and/or lenvatinib can generally be prepared by conventional techniques known to those skilled in the art or by processes analogous to those described in the Schemes and/patent references incorporated herein by using the appropriate isotopically-labelled reagents or starting material instead of the corresponding non-isotopically-labelled reagent or starting material.

Further description and embodiments of combination therapies are provided in the Examples section below.

DETAILED DESCRIPTION OF REPRESENTATIVE EMBODIMENTS

Figure 1B:
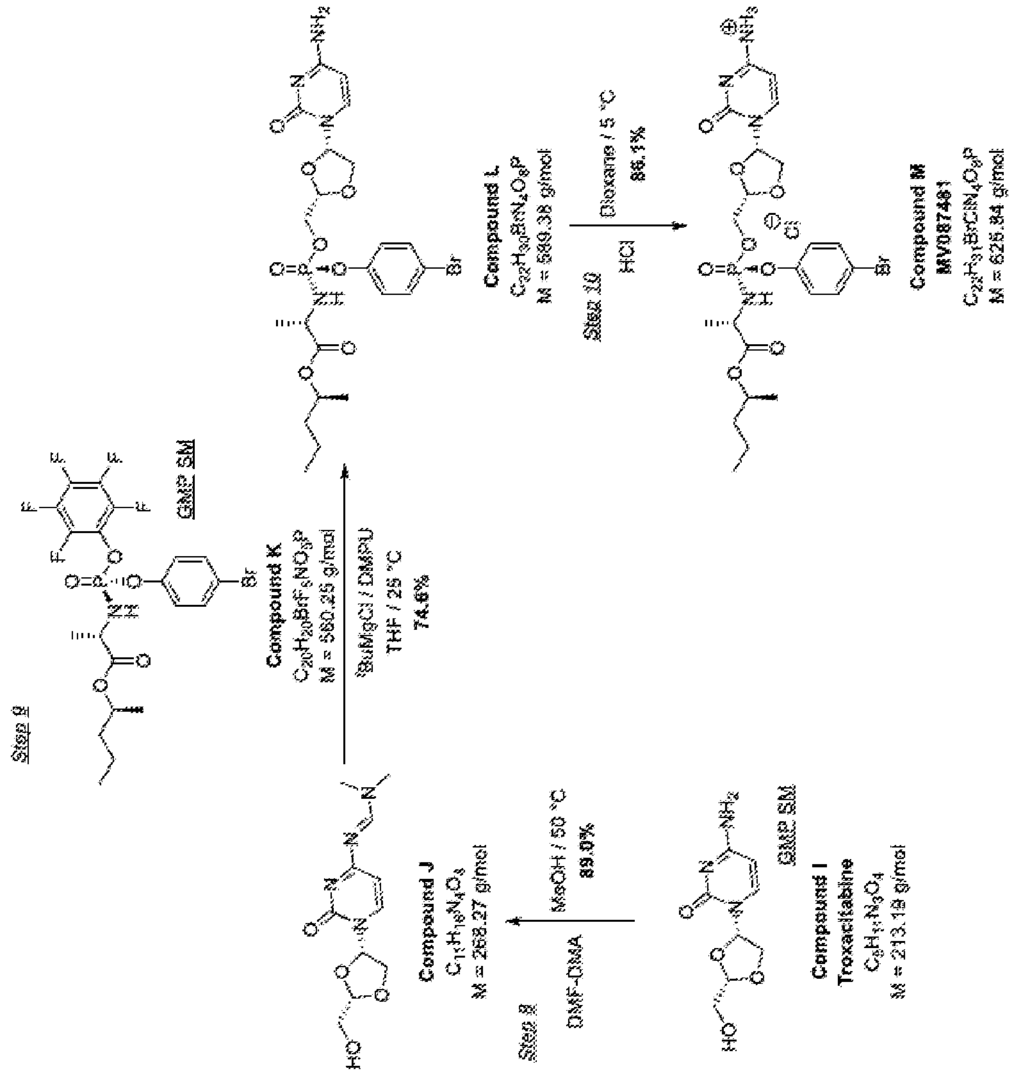

Illustrative embodiments of the invention are described in the following Examples, with reference to the accompanying drawings in which FIGS. 1A and 1B represents a preferred synthesis scheme for the preparation of MIV-818.

Figure 2:
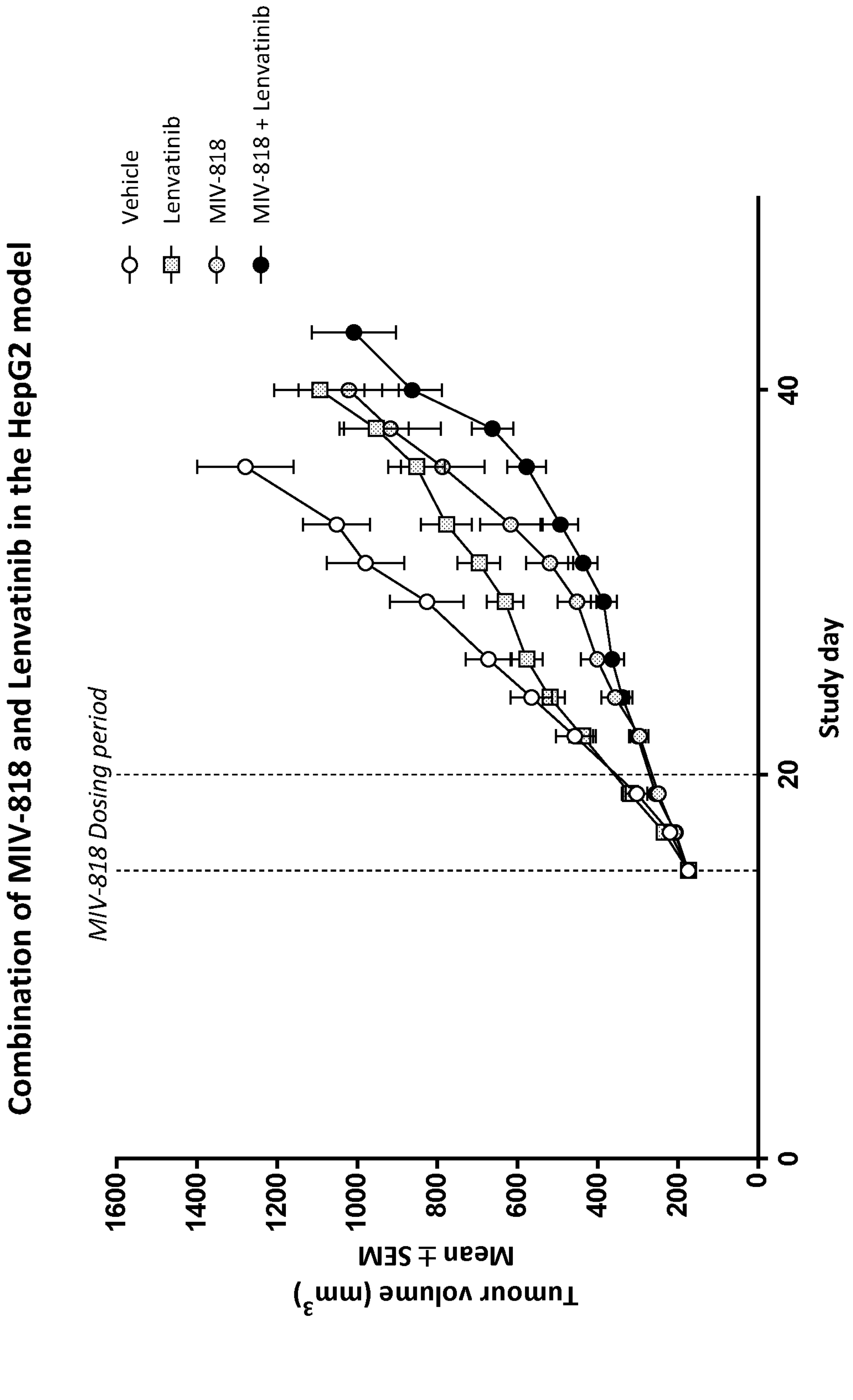

FIG. 2 depicts tumour volume as a function of time in the HepG2 subcutaneous xenograft Example described below.

General Procedure for In Vivo Evaluation of Combinations of Lenvatinib and MIV-818

The effects of MIV-818 treatment in combination with lenvatinib can be assessed in vivo in subcutaneous xenograft models of hepatocellular carcinoma (HCC). The models are based on inoculating HCC cells (e.g. Hep3B, Huh-7 or HepG2) into the flank of immunocompromised mice. Tumour volume is assessed app. three times per week and treatment with compound is typically initiated at a tumour size of 100-200 $mm^3$. A typical study consists of 4 groups (n=10 mice/group);

1) vehicle (control),
2) MIV-818,
3) lenvatinib alone and
4) MIV-818 prodrug in combination with lenvatinib.

MIV-818 is given via oral gavage at doses of 25-100 mg/kg once or twice daily for a period of 5-21 days. Alternatively in view of the rapid metabolism in rodent blood, synergy can be modelled by administering troxacitabine parent intraperitoneally (i.p.) at doses of 2.5-25 mg/kg once or twice daily. Lenvatinib is given via oral gavage once daily at doses of 3-30 mg/kg for a total period of 21 days. Tumour growth is assessed during the course of the treatment period and following cessation of treatment if applicable. Tumour growth inhibition and tumour growth delay is calculated and statistical analysis performed to assess significant effects of treatment compared to the control group.

Experimental Methods

Cell Culture

The HepG2 tumour cells are maintained in vitro with as a monolayer culture in EMEM supplemented with 10% fetal bovine serum at 37° C. in an atmosphere of 5% $CO_2$ in air. The tumour cells are routinely subcultured twice per week by trypsin-EDTA treatment. The cells in an exponential growth phase are harvested and counted for tumour inoculation.

Tumour Inoculation

Each mouse is inoculated subcutaneously at the right flank with Hep G2 tumour cells (1 ×107) in PBS mixed with matrigel (1:1) for tumour development. The date of tumour cell inoculation is denoted as day 0.

Randomization to the different study groups start when the mean tumour size reaches approximately 150 $mm^3$ (100-200 $mm^3$). Typically, 8-12 mice per study group are enrolled in the study. Randomization is performed based on "Matched distribution" method/"Stratified" method using the multi-task method (Study Director™ software). Treatment is started the day after randomization.

Dosing

The preferred delivery route is oral (p.o.). Dose volume of administration is 10 ml/kg (i.e. 0.25 ml for a 25g mouse). The doses of MIV-818 given are between 30 and 100 mg/kg (corresponding to between 48 to 160 μmol/kg). Dosing of Lenvatinib is p.o. 3-30 mg/kg once daily for 21 days.

Dosing is with 1 hour separation between MIV-818 and Lenvatinib (i.e. MIV-818 or Vehicle is given first, followed by Lenvatinib or Vehicle, 1 hour later).

Observation and Data Collection

After tumour cell inoculation, the animals are checked daily for morbidity and mortality. Tumour volumes are measured three times per week in two dimensions using a caliper. A final tumour read is taken for each mouse prior to termination.

Tumour volumes are expressed in $mm^3$ using the formula: "V=(L×W×W)/2, where V is tumour volume, L is tumour length (the longest tumour dimension) and W is tumour width (the longest tumour dimension perpendicular to L). Dosing as well as tumour and body weight measurements are conducted in a Laminar Flow Cabinet.

For comparison between two groups, a Student's t-test is performed. For comparison among three groups, a one-way or two-way ANOVA is performed followed by multiple comparison procedures. All data is analyzed using SPSS 18.0 and/or GraphPad Prism 5.0. $P<0.05$ is considered statistically significant.

EXAMPLE 1

FIG. 1 depicts in vivo tumour growth inhibition (TGI) in the HepG2 model in BALB/c nude mice. Oral dosing was initiated on day 15 with MIV-818 30 mg/kg BID for 5 days and with Lenvatinib 3 mg/kg QD for 3 weeks, as single agents or in combination. The TGI resulting from the combination treatment (MIV-818+Lenvatinib) was significantly improved vs Lenvatinib alone (two-way ANOVA $p<0.0001$).

The invention claimed is:

1. A method of treatment of liver cancer or liver metastases comprising administering to a subject in need thereof a therapeutically effective amount of lenvatinib, or a pharmaceutically acceptable salt thereof in combination with a compound of the formula MIV-818:

MIV-818

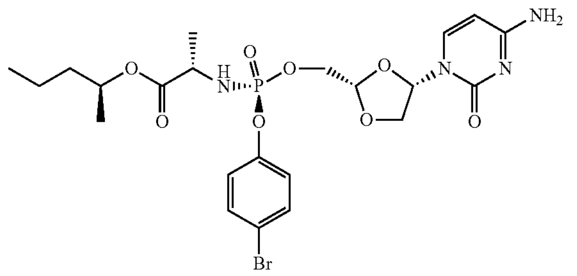 [SMILES: CCC[C@H](C)OC(=O)[C@H](C)N[P@](=O)(OC[C@H]1OC[C@@H](n2ccc(N)nc2=O)O1)Oc1ccc(Br)cc1]

or a pharmaceutically acceptable salt thereof.

2. The method according to claim 1, wherein the lenvatinib and the MIV-818, or pharmaceutically acceptable salts thereof are each administered daily on the same day.

3. The method according to claim 2, wherein the lenvatinib and the MIV-818 or pharmaceutically acceptable salts thereof are co-delivered in a common, orally administered dosage unit.

4. The method according to claim 1, wherein the lenvatinib and the MIV-818 or pharmaceutically acceptable salts thereof are administered as separate, orally administered dosage units.

5. The method according to claim 4, wherein the dosage unit(s) of lenvatinib and the dosage unit(s) of MIV-818 are administered at least 6 hours apart on any given day.

6. The method according to claim 1, wherein the lenvatinib and the MIV-818 or pharmaceutically acceptable salts thereof are alternately administered in monotherapy treatment cycles of 1-28 days.

7. The method according to claim 6, wherein treatment commences with a lenvatinib cycle.

8. The method according to claim 1, wherein the liver cancer is hepatocellular cancer or intra-hepatic cholangiocarcinoma.

9. The method according to claim 1, wherein the liver metastasis is derived from colorectal cancer.

10. The method according to claim 1, wherein the liver metastasis is derived from breast cancer, esophageal cancer, lung cancer, melanoma, pancreatic cancer, or stomach cancer.

11. The method according to claim 1, wherein the lenvatinib and MIV-818 are administered once a day (QB), twice a day (BID), or thrice a day (TID).

12. The method according to claim 6, wherein the monotherapy treatment cycles of 1-28 days are interspersed with treatment-free periods of 1-28 days.

* * * * *